United States Patent [19]  
Eckert et al.

[11] Patent Number: 4,479,939  
[45] Date of Patent: Oct. 30, 1984

[54] METHOD AND COMPOSITION FOR THE TREATMENT OF ACNE

[75] Inventors: Theodor Eckert; Siegfried Nolting; Fritz Kemper, all of Münster, Fed. Rep. of Germany

[73] Assignee: Dr. August Wolff, Chemisch-Pharmazeutische Fabrik GmbH & Co. KG., Bielefeld, Fed. Rep. of Germany

[21] Appl. No.: 445,420

[22] Filed: Nov. 30, 1982

[30] Foreign Application Priority Data

Dec. 1, 1981 [DE] Fed. Rep. of Germany ....... 3147504

[51] Int. Cl.³ .................. A61K 31/00; A61K 31/075; A61K 47/00
[52] U.S. Cl. ...................................... 424/172; 424/338
[58] Field of Search ................ 424/338, 172; 568/566

[56] References Cited

U.S. PATENT DOCUMENTS 2,771,492 11/1956 Chapman et al. .................. 568/566  
3,367,951 2/1968 Nielsen et al. ..................... 568/566  
3,966,787 6/1976 De Jager et al. .................. 568/566  
4,163,800 8/1979 Wickett et al. ..................... 424/326

*Primary Examiner*—Leonard Schenkman  
*Attorney, Agent, or Firm*—Peter K. Kontler

[57] ABSTRACT

Compositions including diacyl peroxides of medium chain fatty acids in the region of $C_6$–$C_{12}$ in a carrier such as an oil/water emulsion or an alcohol gel are utilized for the topical treatment of acne.

Such medium chain, fatty acids formed during the decomposition of diacyl peroxides simultaneously with the release of oxygen are particularly beneficial for the skin.

8 Claims, No Drawings

METHOD AND COMPOSITION FOR THE TREATMENT OF ACNE

BACKGROUND OF THE INVENTION

The present invention relates generally to method and composition for the treatment of acne and, more particularly, to such method and composition where the composition includes a diacyl peroxide of a medium chain fatty acid.

The dermatological term acne broadly denotes a number of different types of disease, the most common of which is *Acne vulgaris* which classically occurs before or during puberty. *Acne vulgaris*, which normally shows itself to be an illness of the sebaceous gland follicle, is constitutional in that it is caused and/or determined by endocrinological, bacteriological and biochemical factors. Androgens and certain estrogens stimulate the growth and function of the sebaceous gland. Shifts in the balance of these sex hormones in either favor and/or increased sensitivity of the sebaceous gland cells due to the influence of the hormones result in excessive sebum production and hypertrophy of the follicle opening. Comedones or "black-heads" consisting of sebum, cell and keratin masses are then formed which block the follicle opening and prevent discharge of the sebum. Sebum lipids penetrate through the fine ruptures of the enlarged follicle wall into the tissue causing lymphatic infection combined with the formation of pustules. This infection is typically caused by the grouping of the free fatty acids of the skin sebum.

Free fatty acids are not primary parts of the sebum but, rather, are formed secondarily during hydrolytic decomposition of triglycerides. The catalyst enzyme is a lipase of bacterial origin formed primarily by the anaerobic, gram positive, propionibacterium acnes which are part of the skin's bacterological flora. Thus, the comedones or "black-heads" contain a large number of the propionibacterium acnes and free fatty acids.

Acne is first observed clinically by the presence of closed and open comedones. When infection develops, *Acne papulo-pustulosa*, with its partially abscessed growths, and serious *Acnes conglobata* with its numerous fused growths develop.

Topical treatment of acne has three objectives:

the removal of the follicle hyperkeratoses and decomposition of the comedones to achieve a keratolytic and a komedolytic effect;

reduction of the acne using antibacterial agents; and retardation of the lipase effect and a reduction of free fatty acids sebostatically.

The conventionally known preparations for the topical treatment of *Acne vulgaris*, some of which contain benzoyl peroxide, have not, to date, achieved these stated objectives. Benzoyl peroxide is a strong oxidizing agent which releases oxygen upon penetration into the follicle and thus creates aerobic conditions in the follicle which retards growth of the anaerobic bacteria. However, during decomposition of the dibenzoyl peroxide simultaneous with the release of oxygen, benzoic acid, a very skin-irritating material, is formed. Therefore, it is evident that the heretofore conventional compositions for the treatment of acne which contain peroxides exhibit considerable side effects, being particularly irritating when applied to the skin. Consequently, in about 10% of the cases, a contact-allergic sensitization occurs due to the topical application of dibenzoyl peroxide.

A primary object of the present invention is to provide a composition which is highly effective in the treatment of different acne forms and which has, even during a longer application period, no deleterious side effects.

SUMMARY OF THE INVENTION

According to this invention, such object is accomplished by providing a composition for the topical treatment of acne which includes a diacyl peroxide of medium chain fatty acids ($C_6$–$C_{12}$) admixed with a carrier.

DESCRIPTION OF THE PREFERRED EMBODIMENT

The application of diacyl peroxides of medium chain fatty acids ($C_6$–$C_{12}$) surprisingly achieved all three objects of conventional cne therapy, i.e., the keratolytic and komedolytic effects, the bacterio-static effect and the sebum-static effect. Diacyl peroxides are also strong oxidizing agents capable of releasing oxygen after penetrating into the follicle thus inhibiting growth of the anaerobic bacteria. In contrast to the benzoyl peroxides, however, the diacyl peroxides simultaneously breakdown with the release of oxygen into appropriate medium-chain, fatty acids, which do not cause an irritation of the skin and other sensitization reactions. On the contrary, such fatty acids are generally skin compatible and possess certain anti-mycetic and anti-bacterial characteristics. Thus, use of diacyl peroxides in long-term applications has proven generally skin compatible with few, if any, skin irritations and sensitization reactions occurring.

Among the group of the diacyl peroxides of the medium chain fatty acids ($C_6$–$C_{12}$), which may be used in accordance with the teachings of the subject invention are didecanoyl peroxide ($C_{10}$) and didodecanoyl peroxide ($C_{12}$). Such peroxides have particularly proven to be best suited for such topical therapy without exhibiting deleterious side effects.

The particular diacyl peroxide should be used in as pure a form as possible. It has been found that a particularly pure diacyl peroxide is obtained, if a concentrated solution of the diacyl peroxide in chloroform is admixed with methyl alcohol in a 2-1 ratio of methyl alcohol to peroxide mixture.

For the topical treatment of acne, incorporation of the diacyl peroxide with a carrier material in a concentration of between about 3%–20% of diacyl peroxide based on the weight of the entire composition has proven to be especially suitable and is therefore preferred. Concentrations of between about 5% and about 10% of diacyl peroxide are particularly preferred. Oil and water emulsions and alcohol gels are particularly preferred carrier materials.

The following examples serve to illustrate certain preferred embodiments of the subject invention and are not to be construed as limiting the scope thereof.

EXAMPLE I

For the treatment of *Acne vulgaris*, a composition including a 5% concentration of didecanoyl peroxide and mixed in an oil/water emulsion was prepared. The composition was applied topically to a subject having *Acne vulgaris* and demonstrated an effective ability to treat such condition.

EXAMPLE II

For the treatment of *Acne vulgaris*, a composition including a 5% concentration of didecanoyl peroxide admixed in an alcohol gel was prepared. When applied topically to a subject having *Acne vulgaris*, the composition was effective in treating the condition with no deleterious side effects.

EXAMPLE III

For the treatment of *Acne vulgaris*, a composition including a 10% concentration of didodecanoyl peroxide admixed in an alcohol gel was prepared. When applied topically to a subject having *Acne vulgaris*, the composition was effective in treating the condition with no deleterious side effects.

EXAMPLE IV

For the treatment of *Acne vulgaris*, a composition including a 5% concentration of didodecanoyl peroxide and mixed in an oil/water emulsion was prepared. When applied topically to a subject having such condition, it was effective in treating same with no deleterious side effects.

Although the foregoing Examples illustrate the preparation of a certain suitable compositions for the treatment of acne, it will be appreciated that other compositions may be used without departing from the spirit and scope of the present invention. Accordingly, the present invention should be limited only by the scope of the appended claims.

What is claimed is:

1. A composition for the topical treatment of acne, said composition including a diacyl peroxide selected from the group consisting of didecanoyl peroxide and didodecanoyl peroxide admixed in a carrier selected from the group consisting of an oil/water emulsion and an alcohol gel, wherein said diacyl peroxide is included in a concentration of between about 3% and about 20% based on the weight of the total composition.

2. The composition of claim 1, wherein said carrier is an oil/water emulsion.

3. The composition of claim 1, wherein said carrier is an alcohol gel.

4. A method of treating acne comprising topically applying to an affected area of the subject an effective amount of a composition consisting of between about 3% and about 20% by weight of a diacyl peroxide of a medium chain, fatty acid ($C_6$–$C_{12}$) and a carrier.

5. The method of claim 4, wherein said diacyl peroxide is didecanoyl peroxide ($C_{10}$).

6. The method of claim 4, wherein said diacyl peroxide is didodecanoyl peroxide ($C_{12}$).

7. The method of claim 4, wherein said carrier is an oil/water emulsion.

8. The method of claim 4, wherein said carrier is an alcohol gel.

* * * * *

UNITED STATES PATENT AND TRADEMARK OFFICE
CERTIFICATE OF CORRECTION

PATENT NO. : 4,479,939

DATED : October 30, 1984

INVENTOR(S) : Theodor ECKERT et al.

It is certified that error appears in the above-identified patent and that said Letters Patent are hereby corrected as shown below:

Foremost page [75] after "Münster," insert --and Hans-Günter Nolden-Temke of Bielefeld, all--.

Col. 2, line 17, change "cne" to --acne--.

Signed and Sealed this

Thirtieth Day of April 1985

[SEAL]

Attest:

DONALD J. QUIGG

*Attesting Officer*  *Acting Commissioner of Patents and Trademarks*